US007297117B2

(12) United States Patent
Trucco et al.

(10) Patent No.: US 7,297,117 B2
(45) Date of Patent: Nov. 20, 2007

(54) METHOD FOR OPTIMIZATION OF TRANSMIT AND RECEIVE ULTRASOUND PULSES, PARTICULARLY FOR ULTRASONIC IMAGING

(75) Inventors: Andrea Trucco, Genoa (IT); Simone Curletto, Genoa (IT)

(73) Assignee: Esaote, S.p.A., Casale Monferrato (IT)

( * ) Notice: Subject to any disclaimer, the term of this patent is extended or adjusted under 35 U.S.C. 154(b) by 209 days.

(21) Appl. No.: 10/852,572

(22) Filed: May 24, 2004

(65) Prior Publication Data

US 2005/0033167 A1 Feb. 10, 2005

(30) Foreign Application Priority Data

May 22, 2003 (IT) .............................. SV03A0023

(51) Int. Cl.
*A61B 8/00* (2006.01)

(52) U.S. Cl. ...................................................... 600/443

(58) Field of Classification Search ........ 600/443–447, 600/455–458; 128/916; 73/625–626, 602
See application file for complete search history.

(56) References Cited

U.S. PATENT DOCUMENTS

| | | | | |
|---|---|---|---|---|
| 5,089,988 | A * | 2/1992 | Arens | 367/12 |
| 5,113,866 | A * | 5/1992 | Hassler et al. | 600/447 |
| 5,517,996 | A * | 5/1996 | Okada et al. | 600/447 |
| 5,551,433 | A * | 9/1996 | Wright et al. | 600/443 |
| 6,279,398 | B1 * | 8/2001 | Bae et al. | 73/625 |
| 6,282,963 | B1 * | 9/2001 | Haider | 73/602 |
| 6,368,279 | B1 * | 4/2002 | Liu | 600/443 |
| 6,436,044 | B1 * | 8/2002 | Wang | 600/443 |
| 6,585,648 | B1 * | 7/2003 | Robinson | 600/437 |
| 6,599,245 | B1 * | 7/2003 | Ma et al. | 600/437 |
| 6,726,631 | B2 * | 4/2004 | Hatangadi et al. | 600/459 |

* cited by examiner

*Primary Examiner*—Francis J. Jaworski
(74) *Attorney, Agent, or Firm*—Woodard, Emhardt, Moriarty, McNett & Henry LLP

(57) ABSTRACT

A method for optimizing transmit and receive ultrasound imaging pulses generates transmit pulses from an array of transducers which are energized by excitation signals that are applied to each individual transducer of the array. Each of the excitation signals are individually weighted to optimize the transducers' contribution to a predetermined energy function. Such optimization may also be performed on the received pulses.

60 Claims, 8 Drawing Sheets

Pressure

Weights

BPP at 30 mm

BPP at 40 mm

BPP at 50 mm

BPP at 60 mm

METHOD FOR OPTIMIZATION OF TRANSMIT AND RECEIVE ULTRASOUND PULSES, PARTICULARLY FOR ULTRASONIC IMAGING

CROSS-REFERENCE TO RELATED APPLICATION

The present application claims the benefit of Italian Application Serial No. IT SV2003A000023, filed on May 22, 2003, which is hereby incorporated by reference in its entirety.

BACKGROUND OF THE INVENTION

The invention addresses a method for optimizing ultrasonic transmit and receive pulses, particularly for ultrasound imaging, wherein transmit pulses are generated from ultrasonic pulse contributions of each of a plurality of electroacoustic transducers, which are grouped in an array and are individually triggered by electric excitation signals, the excitation signal being applied to each individual transducer of the array with a predetermined delay with respect to the application of the excitation signal to the other transducers, and a weight being applied to the excitation signal of each transducer for increasing/decreasing the amplitude of the excitation signal and, as a result, the acoustic signal generated by the transducer.

In prior art insonification and ultrasonic pulse generation methods for ultrasonic imaging, each pulse results from ultrasonic pulse contributions of a certain number of electroacoustic transducers which are individually excited to transmit the corresponding acoustic pulse at different times, i.e. with predetermined delays relative to each other, to generate a comprehensive pulse which is focused on a predetermined scan line or band in the direction of the body or object under examination, and at a predetermined penetration depth within said body or object under examination.

In addition to said focusing, the application of amplitude attenuating/increasing weights to the individual acoustic pulse contributions provided by transducers is known, in order to obtain beam patterns, i.e. pulse fronts having a narrow main lobe, having a predominant amplitude as compared with side lobes. This has the purpose of reducing insonification in regions of the body or object under examination that are close to those on which the ultrasonic transmit pulse is focused and of reducing artifacts in images. Essentially, the side lobes generate reflection pulses from the areas adjacent to pulse focusing areas, and thereby contaminate or distort to a certain extent the resulting image by superposition of such pulses upon the reflection pulses deriving from the main lobe and from the ultrasonic pulse focusing area on the body or object under examination.

Nevertheless, in prior art no consideration is given to the problem that such optimization process does not account for the effects on mechanical pressure distribution in the body or object under examination, which is not optimal in itself, and becomes even less homogeneous in the focusing region, as a result of the ultrasonic pulse optimization process as described above.

The mechanical pressure that is exerted in the body or object being examined also has a certain importance, an excessive mechanical pressure potentially causing the structure of the material of the body or object under examination to break. Such effect is particularly undesired in the field of biomedical imaging, the tissues of the body or object under examination being frequently permeated with contrast agents to enhance visibility of non echogenic tissues. These contrast agents are made of microspheres or microbubbles, which have a nonlinear reflection behavior and reflect the acoustic signal at a frequency that is different from that of the incident transmit pulse, thereby allowing to image structures of non echogenic materials or tissues.

Contrast agents are particularly responsive to the mechanical pressure exerted by acoustic insonification pulses and may be destroyed when such mechanical pressure exceeds predetermined limits.

Essentially, when considering the mechanical pressure profile generated along the scan line on which the ultrasonic pulse is focused, at depths different from the focusing depth, the mechanical pressure value is found to change with depth. Since contrast agents may be located along a scan line at different positions as compared with the ultrasonic pulse focusing depth, prior art methods cannot ensure that the ultrasonic pulse has the right mechanical pressure in the area that is permeated with contrast agents, and it is further not easy to predict if such pressure will be lower or higher than the maximum allowed pressure to prevent contrast agent destruction. Also, regarding the beam pattern, prior art methods cannot ensure that the latter will be constant or substantially constant or anyway that it will maintain a good quality as the penetration depth of the ultrasonic pulse within the body or object under examination changes.

BRIEF SUMMARY OF THE INVENTION

Therefore, the invention has the object of providing a method for optimization of transmit and receive ultrasound pulses, particularly for ultrasonic imaging, whereby the transmit ultrasound pulse may be optimized along a scan line or band, on which the pulse is focused, and across a predetermined penetration depth range, which spans or contains the focusing depth, in such a manner as to obviate the drawbacks of prior art methods, thereby providing both mechanical pressure optimization and beam pattern optimization.

The invention fulfils the above objects by providing a method for optimization of transmit and receive ultrasound pulses, particularly useful for ultrasonic imaging.

The optimal desired mechanical pressure profile relative to the penetration depth of the ultrasonic pulse within the body or object being examined is defined as a function of at least the amplitude weighting parameters for the transducers' contributions to the comprehensive pulse, and of the transmission excitation delays for individual transducer pulse contributions in order to focus ultrasonic pulses on a scan line or band and at a certain penetration depth within the body or object under examination.

The ideal beam pattern for ultrasonic pulses relative to the propagation time or penetration depth within the body or object under examination is defined as a function of at least the amplitude weighting parameters for the transducers' contributions to the comprehensive pulse, and of the transmission excitation delays for individual transducer pulse contributions in order to focus ultrasonic pulses on a scan line or band and at a certain penetration depth within the body or object under examination.

An energy function which depends on the difference between the ideal pressure profile and the actual pressure profile and between the ideal beam pattern and the actual beam pattern is defined and the minimum of that energy function is determined.

Weighting parameters and delays which correspond to the minimum of the energy function are determined and used to excite the transducers to generate the comprehensive ultrasonic pulse.

The transducer excitation delays may be chosen to be ultrasonic pulse focusing delays, which are currently used for focusing ultrasonic pulses in ultrasonic imaging apparatus.

An additional variable may be provided for the individual transducers' pulse contributions which form the comprehensive ultrasonic pulse. The transducers of the transducer array, individually or in subgroups, may be excited to transmit pulse contributions having different waveforms. In this case, both the function that describes the pressure profile relative to the penetration depth and the function that describes the beam pattern profile may depend on the waveforms of the individual transducers' contributions.

DESCRIPTION OF THE DRAWING

The method of the invention will be described below with reference to a few experimental embodiments, whose results are shown in the annexed figures, in which.

DESCRIPTION OF THE EMBODIMENTS

Figure 1:
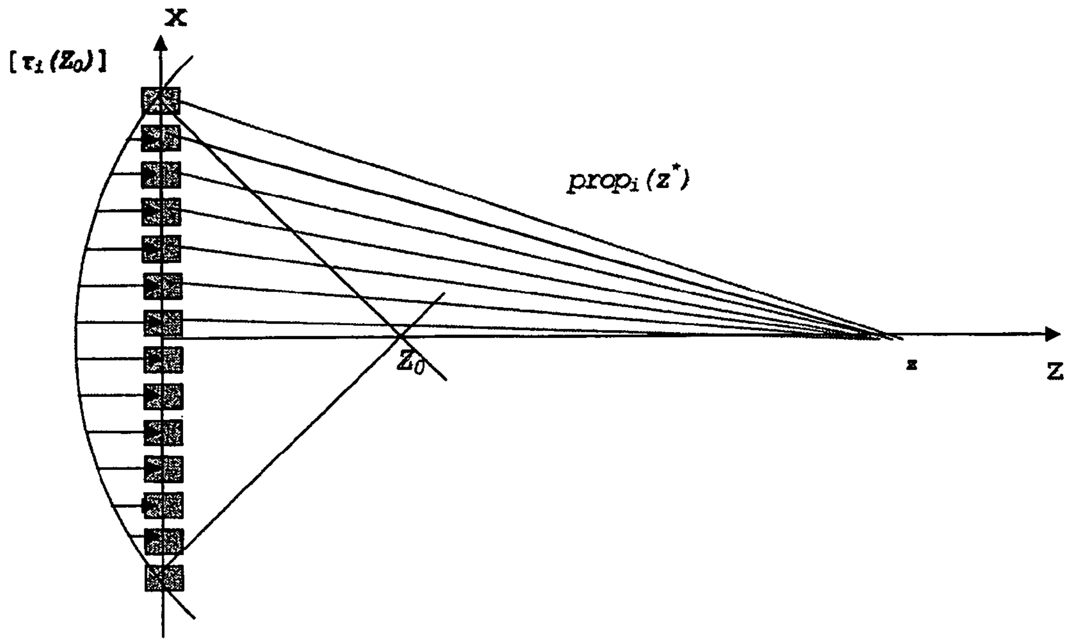
FIG. 1 is a schematic view of an array of transducers, and the propagation geometry of an ultrasonic pulse which is focused on a scan line in the pulse propagation direction within a body under examination.

The optimization goal for forming ultrasonic pulses is a compromise between the achievement of the best beam pattern and the achievement of the best mechanical pressure profile. Although there is not an exact mathematical solution, there certainly exists a best solution, wherein the energy function is minimized. Due to the considerable computational load required by the large number of variables, the optimal solution is obtained by using predictive or optimization algorithms of the stochastic or evolutionary type.

Suitable algorithms for this application are genetic algorithms, e.g., the Tabu search, among others. A particular algorithm that provides effective results, i.e., a relatively fast convergence and solution stability, where slight parameter variations with respect to the best solution generate slight result variations, is the Simulated Annealing algorithm.

This algorithm is described in "Genetic Algorithms in Search, Optimization and Machine Learning" by D. E. Goldberg, AddisonWesley, Reading, Mass., 1989, and in "Simulated Annealing: Theory and Applications" P.J.M. by van Laarhoven and E. H. L. Aarts, Kluwer Academic Publisher, Dordrecht, 1987. A description of the Tabu search is provided in "A user's guide to Tabu search" by F. Glover, E. Taillard, D. de Werra, published in Vol. 41 of Annals of Operations Research, printed in 1993 by J. C. Baltzer AG.

The energy function may be expressed in various manners. In general terms, the energy function has the following general form:

$$E(W,\tau,\omega)=\int_z [Pcal_i(W,\tau,\omega,z)-Pdes(z)]^2 dz+\int_x\int [BPcal_i(W,\tau,\omega,z,x)-BPdes(z,x)]^2 dx dz$$

where:

Pdes(z)is the function that describes the desired pressure profile at the different penetration depths along the propagation axis x of the ultrasonic pulse.

$Pcal_i(W,\tau,\omega,z)$is the function that describes the pressure profile as determined from the weight vector, the delay vector and the waveform vector at the ith iteration of the minimization vector and at the different penetration depths along the ultrasonic pulse propagation axis z, relative to the weight vector W, the delay vector θ and the waveforms of the pulse contributions generated by the transducers θ.

BPdes(z,x) is the function that describes the desired beam pattern at the different penetration depths along the ultrasonic beam propagation axis z.

$BPcal_i(W,\tau,\omega,z)$ is the function that describes the beam pattern as determined from the weight vector, the delay vector and the waveform vector at the ith iteration of the minimization vector and at the different penetration depths along the ultrasonic pulse propagation axis z, relative to the weight vector W, the delay vector θ and the waveforms of the pulse contributions generated by the transducers θ.

Both the desired mechanical pressure profile and the desired beam pattern may be defined in numerical terms. Furthermore, the energy function may be easily discretized and integrals be transformed into a summation, by assuming a certain approximation error margin.

The above function is a generally expressed energy function and may be slightly changed by using coefficients whereby the contributions to said function of the beam pattern optimization portion and of the mechanical pressure optimization portion, as represented by the corresponding integrals, may be further weighted.

Regarding the ranges wherein the propagation depth variable z and the variable x, which is defined along an axis parallel to the transmission surface of the array of electroacoustic transducers may change, the variable z may obviously change in a range of interest which spans the ultrasonic pulse focusing depth, or in a range in which the focusing depth is one of the upper or lower limits or is close to one of said limits.

Conversely, the variable x may be in a range that is equal to or larger than the whole extension of the transducer array along the x axis parallel to the transmit surface of said transducer array, or said range may be smaller than said extension of the transducer array along the x axis and of the same order of magnitude as a scan band corresponding to a few parallel and adjacent scan lines.

It shall be noted that the energy function to be minimized describes an energy also in physical terms, as it represents the surface difference in a velocity range, which strengthens the adequateness of the above energy function.

According to a further improvement, in the calculation of weights and possibly delays and/or waveforms of transducers' contributions, account is taken of the fact that, for instance, the attenuation of the ultrasonic pulse within the body or object under examination does not only depend on the physical characteristics of the signal, but also on the structure of the body which, e.g. in ultrasonic imaging applications may vary from one region to another due to the presence of different biological tissues, having different ultrasonic pulse absorption capacity. Signal attenuation occurs due to the geometry of the propagation condition, to an attenuation caused by tissue absorption, for instance in biomedical imaging and also due to the radiation pattern of each probe element.

As is further detailed in the following description of an embodiment of the method, it was surprisingly found that the results derived from the generation of an ultrasonic pulse having a nearly constant mechanical pressure in the expected propagation depth range and a beam pattern with a narrow, scan-line centered main lobe and low side lobes, far from the main lobe, which pattern is constant with time, i.e. along the ultrasonic pulse propagation axis, are considerable even when using focusing delays like those conventionally in use in ultrasonic transducer arrays, such as ultrasonic probes, by generating transducers' contributions to the ultrasonic pulse which have the same waveform, of the conventional type, and by only using amplitude weights for said array transducers' contributions. Also, ultrasonic pulse attenuation hypotheses may be only limited to geometric attenuation during propagation.

This provides a considerable simplification of the method as well as remarkable mechanical pressure and beam pattern improvements as compared with prior art, while reducing the computational load. In certain special cases, the method may be required to be carried out by contemplating all possible variables, i.e. in its most general and widest form.

For optimization of receive pulses, the principles that were used for transmit pulses also apply. However, for reception, the waveform variable of the transducers' contributions to the ultrasonic pulse is irrelevant, as the receive contributions consist of the transmit contributions reflected by the structure of the material that forms the body or object being examined. The receive focusing delays may be also kept substantially identical to those conventionally in use for receive beam forming.

For reception also, the only variable for optimization consists of the components of the weight vector.

An improvement of the method according to this invention provides a further simplification of the combined transmit and receive optimization.

Such improvement accounts for the fact that, in order to optimize the ultrasonic transmit pulse, mechanical pressure is particularly relevant, as it particularly exerts its action on contrast agents during transmission of the ultrasonic pulse whereas the provision of an ideal beam pattern or a beam pattern as close as possible to the ideal is not critical to image quality because reflection signal contributions from regions of the body under examination close to those along the focusing line or band can be removed or anyway drastically attenuated by acting on the optimization of reflection pulse reception by the electroacoustic transducers of the array. In fact, if receive ultrasound pulses are optimized by defining a weight vector according to the method of receive pulse beam pattern optimization and in the sense of obtaining a receive pulse having a narrow main lobe and far and low-amplitude side lobes, the contributions to the reflected signal due to reflections from regions of the body close to those along which focusing of the ultrasonic pulse from the side lobes of a transmit pulse having an acceptable but not optimal beam pattern are automatically removed or drastically attenuated. In ultrasonic imaging this has an effect on the image, which is not soiled, i.e. is free from artifacts and has a good side resolution. Conversely, pulse mechanical pressure optimization has no relevance because the mechanical pressure of the transmit pulse is certainly higher than that of the corresponding reflection pulse, hence any destruction effect of an excessive mechanical pressure, e.g. on contrast agent microbubbles, would already occur upon transmission of the ultrasonic pulse and during propagation thereof within the body under examination, whereby the reflected acoustic wave range has an insignificant effect or no effect at all.

Thanks to this discovery, the optimization method of the invention may be further simplified, by providing a combined transmit and receive optimization wherein the amplitude weights of the individual pulse transducers' contributions are determined for only minimizing the mechanical pressure part of the energy function, i.e. the first integral of the above function, whereas, upon reception, amplitude weights are applied to the signals emitted from the transducers, which weights are determined by only minimizing the beam pattern part of the energy function, i.e. the second integral of the above energy function.

In stricter terms, upon transmission the amplitude weights of individual electroacoustic transducers' contributions to the transmit pulse are determined by minimizing the following function:

$$E(W, \tau, \omega) = \int_z [Pcal_i(W, \tau, \omega, z) - Pdes(z)]^2 dz$$

whereas, upon reception, the amplitude weights of the individual electroacoustic transducers' contributions to the receive pulse are determined by minimizing the following function:

$$E(W, \tau) = \int_x \int [BPcal_i(W, \tau, \omega, z, x) - BPdes(z, x)]^2 dx dz$$

in which the beam patterns (designated as BP) are those related to ultrasonic pulse reception. As optimization of pulse waveforms is no longer possible upon reception, the variable θ was omitted from the energy function E.

Once more, the possibility shall be considered of simplifying as much as possible the method by using, upon transmission, pulse contributions of transducers having the same waveform θ and by using, as transmit and receive delays, the delays θ that are commonly used for ultrasonic imaging, which allows to omit the variables θ, θ in the above equations, by replacing them with constants.

Furthermore, thanks to the possibility of implementing, upon reception, the so-called dynamic focus technique, which maintains the focus of contributions from different depths, integration relative to the variable z is no longer required. In fact, the receive beam pattern as determined at a given depth can represent the beam patterns determined at other depths, which are approximated with a satisfactory precision. Therefore, the last equation can be further simplified as follows:

$$E(W) = \int_x [BPcal_i(W, \tau, \omega, z_0, x) - BPdes(z_0, z)]^2 dx$$

Referring to the above equations, a great number of variants may be provided, which are all aimed at making the beam pattern or the pressure profile as close as possible to the desired ones, by optimization of the specified parameters. An exemplary, non limiting list of possible variants includes:

(i) integration of the absolute values of differences instead of the squares of differences;

(ii) integration of x and/or z variables over limited intervals to only consider, for instance, the main lobe or the side lobes;

(iii) replacement of the desired pressure profile and/or the desired beam pattern with a constant, possibly null, which represents, for instance, average values over the integration interval being considered;

(iv) integration of excess values, if any, resulting from the difference between what was actually obtained and what was desired, the latter term being assigned the meaning of maximum limit;

(v) replacement of integral operators with different, possibly nonlinear, operators, such as a mean operator or a maximum value operator;

(vi) integration carried out with respect to variables different from and direction/distance polar coordinates instead of the Cartesian coordinates x and z, or arbitrary variables (which are defined by using the sinus of the relevant angles), which provide an optimization that may apply to any steering angle of the scan line;

(vii) any suitable combination of the above.

For instance, with reference to the beam pattern, an energy function may be created that sums the integral of the square differences between obtained and desired values in the region of the side lobe, and the integral of the excess values with respect to a maximum level in the side lobe region. Otherwise, referring to the pressure profile, an energy function may be generated which accounts for pressure variance within the z interval being considered.

Referring to FIG. 1, the individual squares along the x axis represent the individual transducers of a transducer array. The z axis defines the propagation direction perpendicular to the transmitting surface of transducers. The delays θi, where i designates the ith transducer are first calculated as a function of focusing on a point $Z_0$ along the z axis. In this embodiment, the propagation direction is parallel to the x axis, hence the other directional parameter, i.e. the theta angle is zero. In order to determine the pressure in the general point Z*, in addition to the delays associated to a purely geometric function which determines focusing on said point $Z_0$, account shall be further taken of the propagation time to reach the point Z*, in this case on the z axis.

In the experiment whose results are shown hereafter, the delay determination function is generally known and widely used in ultrasonic imaging apparatuses and is not further changed for optimization.

The experiment was carried out by using an ESAOTE PILA 532 probe. The latter is a Linear array 128 transducer array. The transmission carrier frequency is of 5.56 MHz, the mechanical focus of the probe is 25 mm and the pitch is of 0.245 mm.

For transmission an energy function was defined, from whose minimization an amplitude weight was determined for each transducer's contribution to the comprehensive transmit pulse.

The energy function that was used is as follows:

$$E(W, \tau, \omega) = \int_z [Pcal_i(W, \tau, \omega, z) - Pdes(z)]^2 dz$$

where Pdes(z) is the function that describes the desired pressure profile at the different penetration depths along the propagation axis x of the ultrasonic pulse.

$Pcal_i(W,\tau,\omega,z)$ is the function that describes the pressure profile as determined from the weight vector, the delay vector and the waveform vector at the ith iteration of the minimization vector and at the different penetration depths along the ultrasonic pulse propagation axis z, relative to the weight vector, the delay vector θ and the waveforms of the pulse contributions generated by the transducers θ.

Minimization was carried out by using a known stochastic algorithm known as Simulated Annealing whereof detailed sources are indicated above.

For the determination of weights, the geometric attenuation of the transmit pulse was only considered, whereas attenuations caused by the structure of the material of the body under examination and by the radiation patterns of the different elements of the probe being used were not accounted for.

Figure 2:
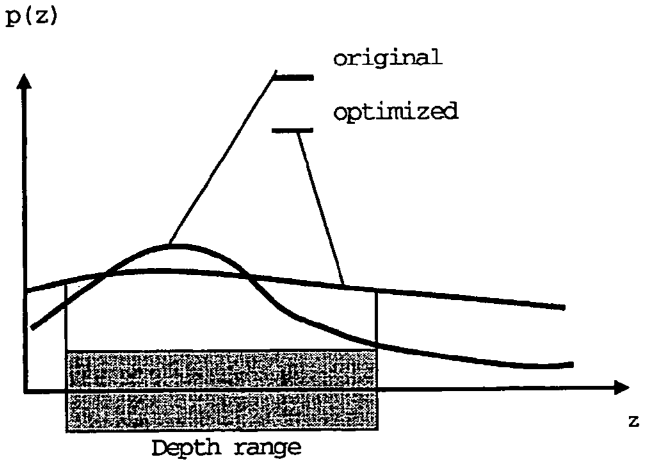
FIG. 2 is a schematic example of the actual and desired mechanical pressure profiles along a scan line, and relative to the z axis parallel to the ultrasonic pulse propagation direction.

FIG. 2 shows a hypothetical comparison between the mechanical pressure profile as generated by the non optimized pulse and relative to the pulse penetration depth within the body under examination along the z axis and the desired mechanical pressure profile within the region of interest along the z axis, i.e. between two different penetration depths.

Figure 3:
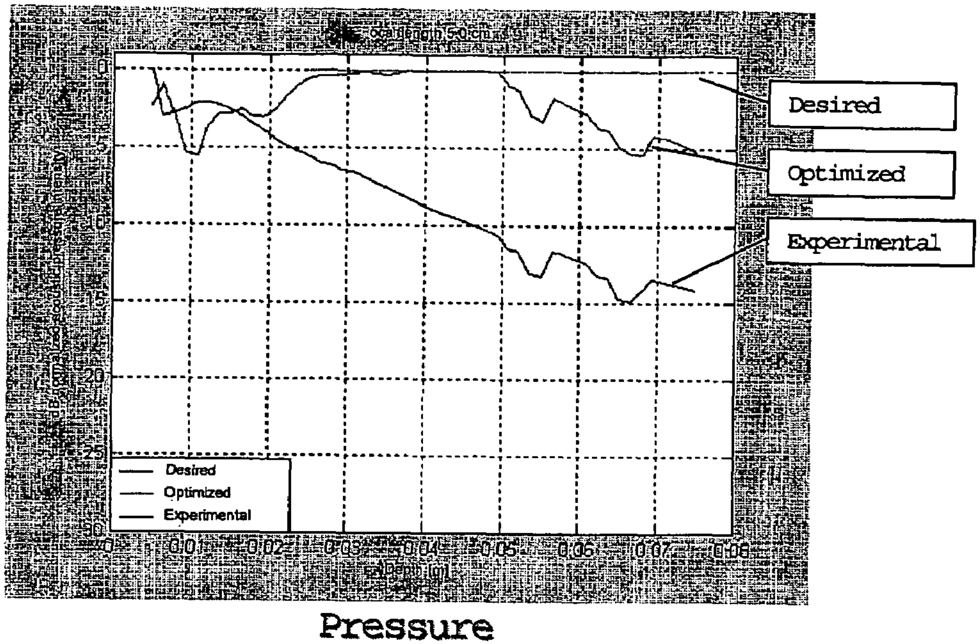
FIG. 3 is a chart of mechanical pressure profiles, as desired, optimized and non optimized, relative to the penetration depth.

FIG. 3 is a chart that shows the comparison between desired, optimized and experimental, i.e. non optimized mechanical pressures. Note that the mechanical pressure of the transmit pulse is substantially constant and coincident with the desired pressure within the penetration depth range of interest.

Figure 4:
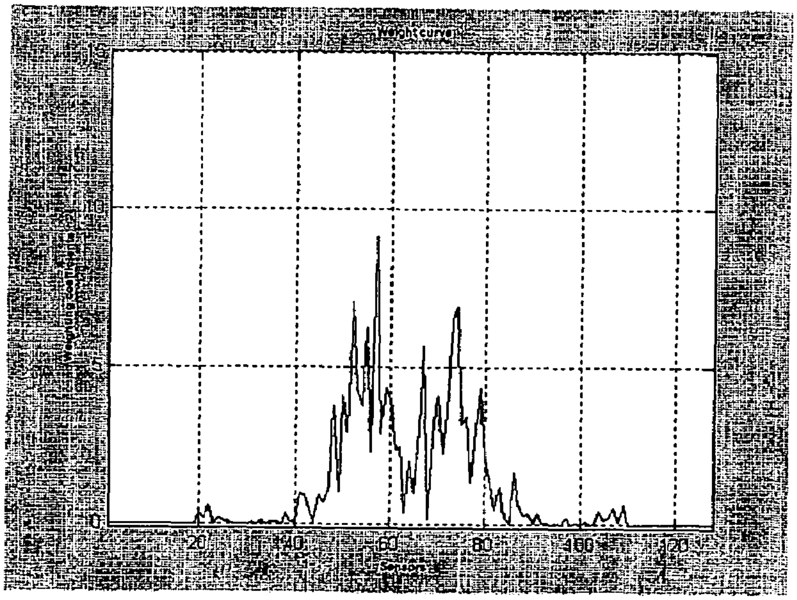
FIG. 4 shows the curve of weights with reference to the individual transducers of the transducer array.
Figure 5:
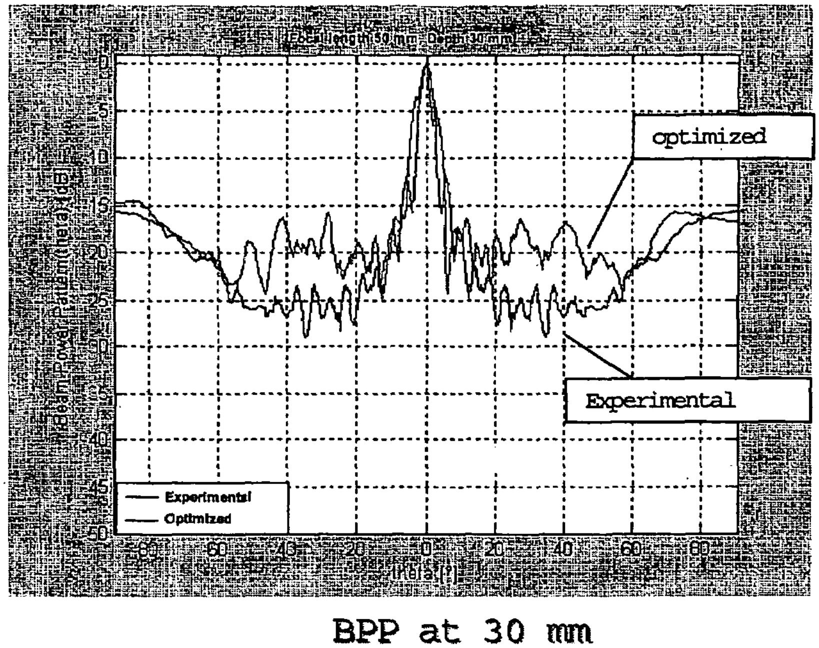
FIGS. 5 to 8 show charts of the original beam pattern and a pattern optimized at different transmit pulse penetration depths.
Figure 6:
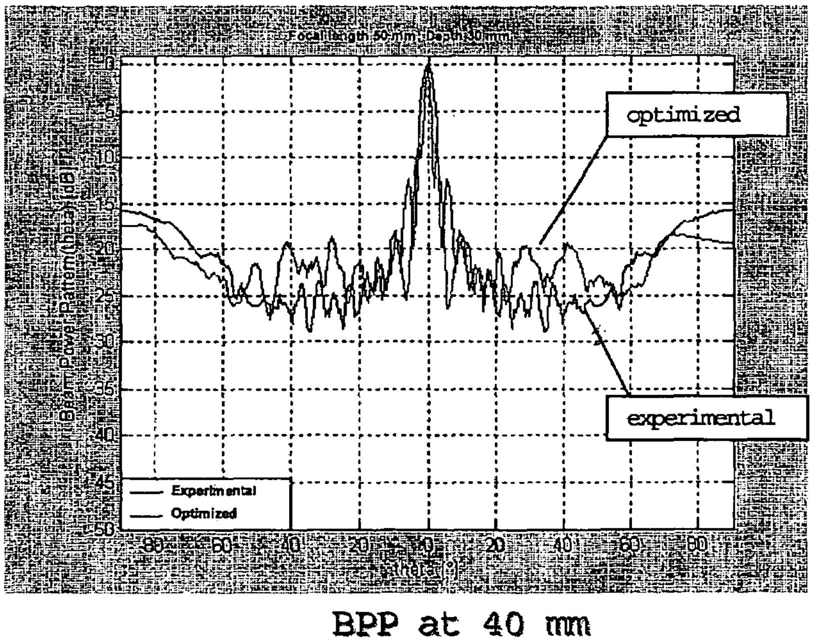
Figure 7:
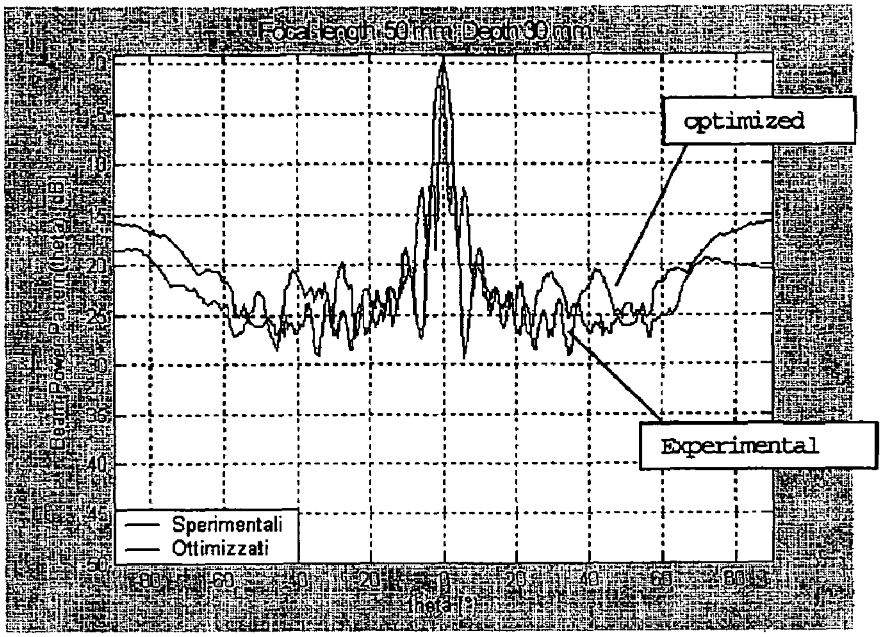
Figure 8:
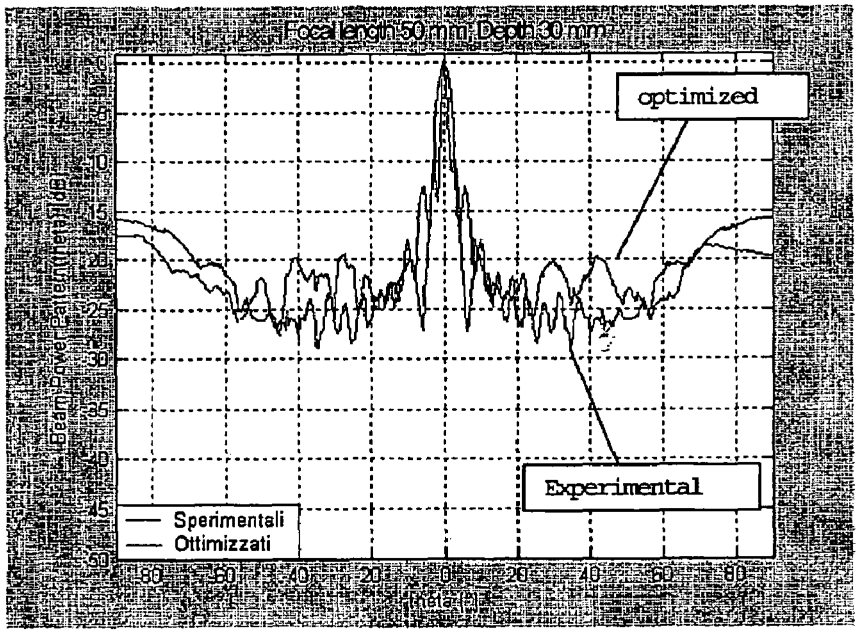

FIG. 4 shows the amplitude weights as determined by minimizing the above energy function, relative to the corresponding transducers of the array.

In this experiment, both the waveforms of the contributions of transducers to the pulse and the conventionally determined delays were considered as constant and the only variable to be determined by minimizing the energy function was the vector of amplitude weights for said pulse contributions of the individual transducers to the ultrasonic pulse.

While optimization did not account for the ultrasonic pulse beam pattern in the energy function, but only for the mechanical pressure in the penetration depth range of interest, FIGS. 5 to 8 show the beam pattern at different penetration depths within the body under examination both for the optimized pulse and for the experimental pulse, i.e. provided by the probe in normal conditions, with no optimization according to the inventive method.

The results were tested for stability against perturbation of weights or pulse features. Such analysis was carried out while perturbing the system with several different types of noise. The optimization as obtained with the inventive method was found to be stable, in that slight perturbations only generated slight or little variations of mechanical pressure and/or beam pattern characteristics, as compared with optimized, non perturbed ones.

Figure 9:
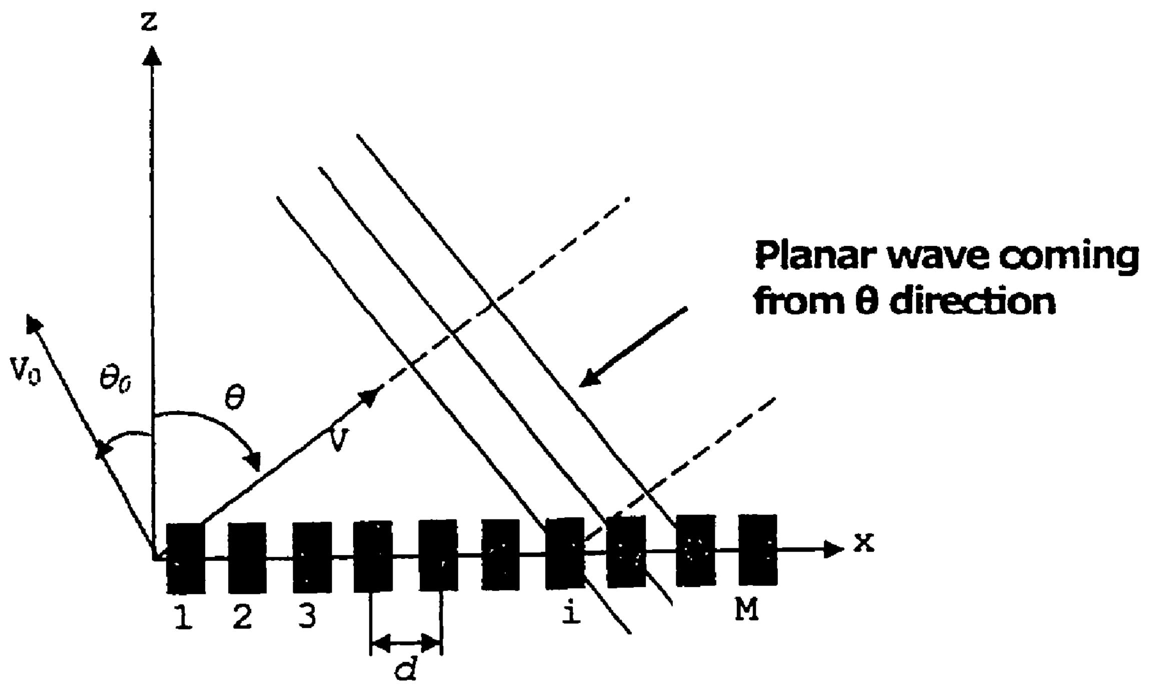
FIG. 9 shows a diagram of the geometry whereon receive beam forming is based.

FIG. 9 is a schematic view of the condition of an array of transducers in the case of receive beam forming, i.e. the geometric conditions which lead to the determination of receive delays.

The hypothesis is that of a broad band, far field beam forming; this hypothesis is widely acceptable because, although medical ultrasonic imaging acts in near field regions, the well known dynamic focusing technique allows to work, all over the region under examination, in conditions that are very close to typical far field conditions. In the Figure the following symbols designate: $\theta_0$: the steering direction; $v_0$: the steering unit vector; θ: the arrival direction; v: the arrival unit vector; d: the distance between elements (pitch); 1, 2 . . . i, . . . , M: the sensors of the array.

In the far field hypothesis, the whole Beam Pattern (BP) formulation may be made with respect to the independent variable u, which is defined as:

$$u=\sin(\theta)-\sin(\theta_0)$$

Therefore, in the following charts, the beam pattern profiles will be always indicated with reference to the above u variable.

The experiment was carried out by using an ESAOTE PA230e probe. The PA230e probe is a Phased array 128 transducer probe. It has a carrier frequency of 2.5 MHz, a 100 mm mechanical focus, a pitch of 0.17 mm; Upon transmission it has a 90 mm focus (depth), and a Focal Number of 1.5.

Referring to the above, constant delays were used, i.e. those well known in ultrasonic imaging. Waveforms have no influence upon reception, as mentioned above. Therefore, optimization was carried out with the aim of determining the vector of the amplitude weights that provide a minimum of the following energy function:

$$E(W)=\int_u [BPcal_i(W,\tau,\omega,u)-BPdes(u)]^2 du$$

where:

BPdes(u) is the function that describes the desired beam pattern as a function of said arbitrary variable u, whose possible values are of −2 to +2, which allows to account for all possible steering angles. In this case, integration was carried out for u values of 0 to 1.2.

$BPcal_i(W,\tau,\omega,u)$ is the function that describes the beam pattern that was calculated on the basis of the weight vector, the delay vector and the waveform vector, at the ith iteration of the minimization algorithm and as a function of said arbitrary variable u.

Receive optimization was carried out by only considering the beam pattern of the received pulse, and not the mechanical pressure thereof. This is possible because mechanical pressure substantially affects the material structure of the body under examination during transmission only.

On the other hand, beam pattern optimization has the purpose of ensuring an optimal side resolution and of suppressing the artifacts caused by signals reflected by regions of the body under examination adjacent to pulse focusing regions, which are mainly due to the presence of side lobes that are too enhanced and/or close to the main lobe of the pulse.

Here, optimization may be effected on reception, and not only on transmission. In fact, beamforming, which may be considered as a spatial filter, allows to isolate the echoes backscattered from the scene in the steering direction $\theta_0$, from all echoes received from all possible directions θ.

Therefore, this technique allows to suppress or drastically attenuate the signal contributions associated to side lobes.

Figure 10:
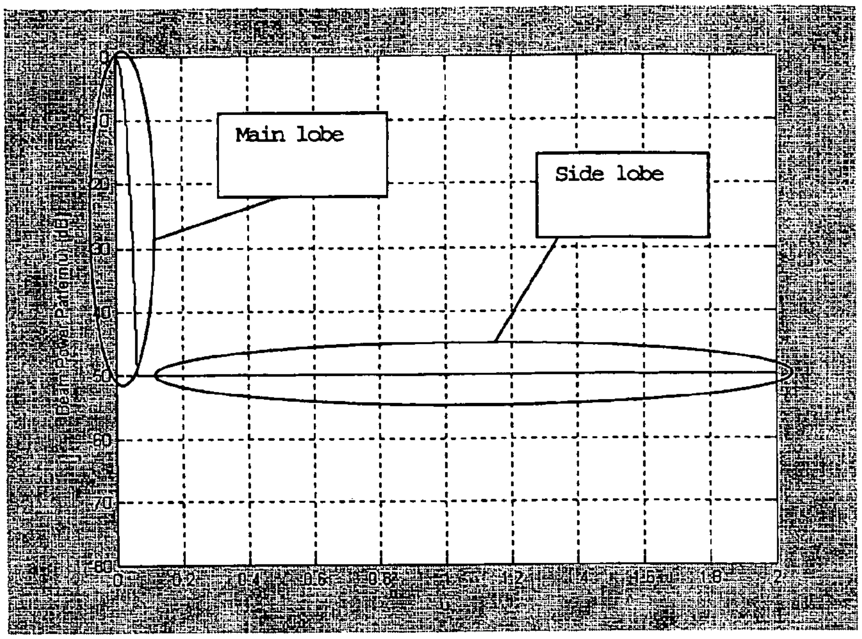
FIG. 10 is a chart of the desired beam power pattern, relative to the u variable, which is defined as $\sin(\theta)\sin(\theta_0)$, such angles being defined in FIG. 9.

FIG. 10 is a chart of the desired beam pattern setting function.

Figure 11:
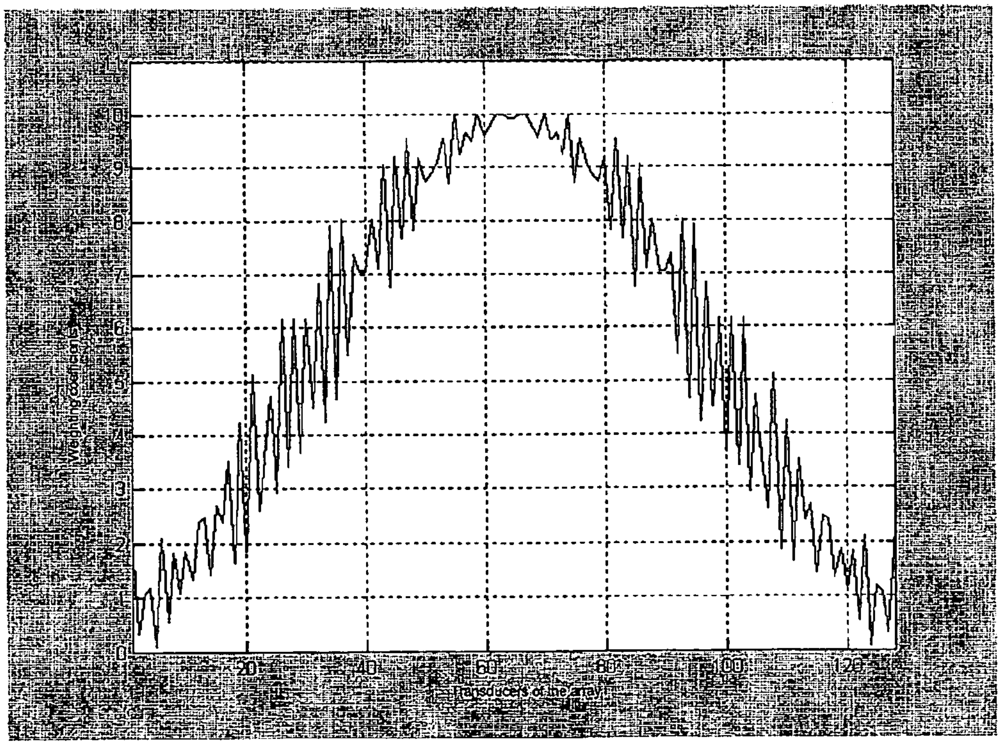
FIG. 11 shows the function for determining the amplitude weights relative to the individual transducers, as obtained by the optimization according to the present method.

By minimizing the above energy function, an amplitude weight vector is obtained, for the signal contributions of each transducer to the comprehensive receive signal, which are designated in the chart of FIG. 11.

Figure 12:
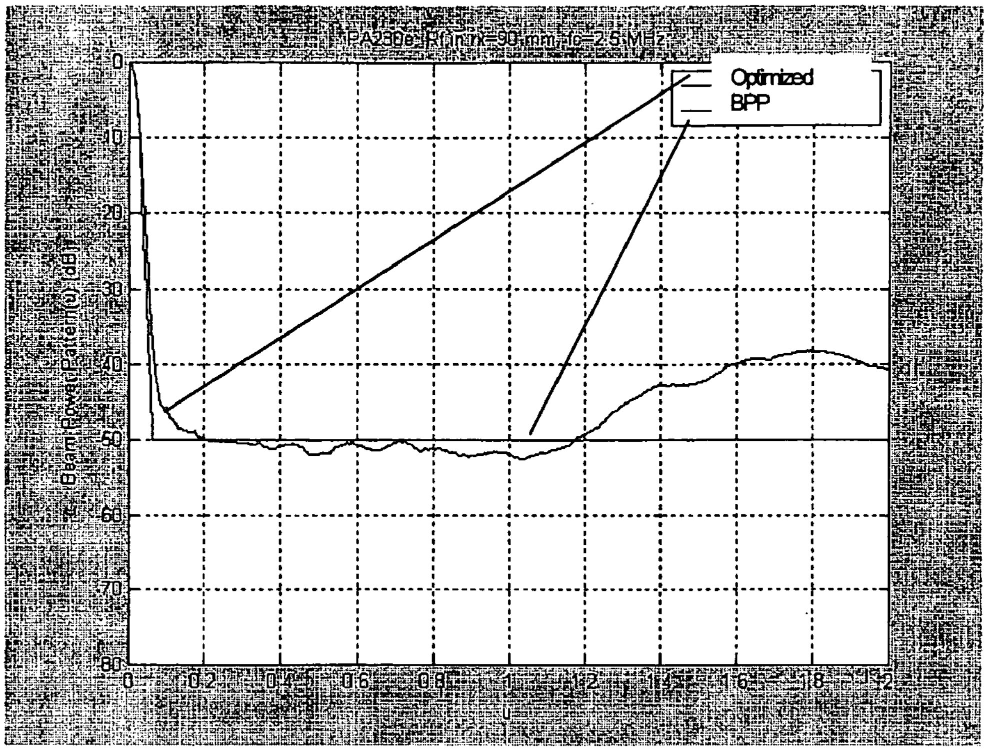
FIG. 12 shows a chart in which the desired beam power pattern is compared with the beam power pattern of the receive pulse, which is optimized with reference to the amplitude weights of the signal contributions of each receive transducer.

FIG. 12 shows the result of the beam pattern, as optimized by using the weights as shown in FIG. 11, which were determined by the inventive method, and in comparison with the desired beam pattern.

Figure 13:
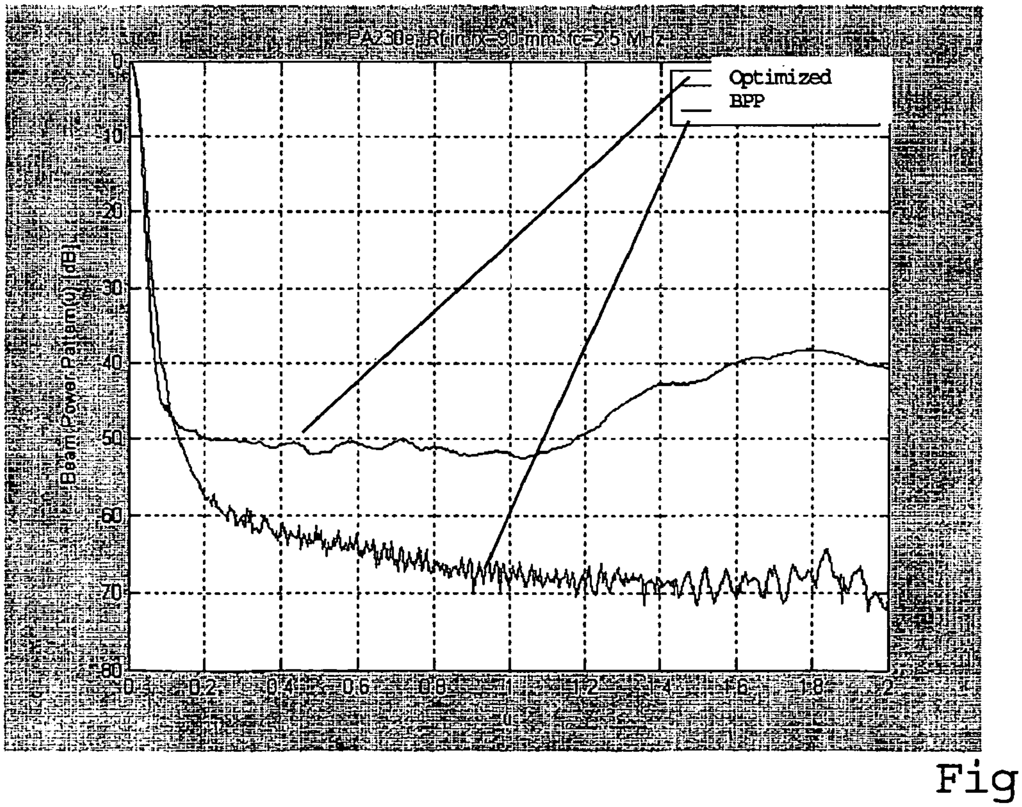
FIG. 13 is a chart like that of FIG. 12, in which the beam power pattern of both the optimized signal and the original signal, which is not optimized with the method of the invention.

FIG. 13 shows, like FIG. 12, the optimized beam pattern as compared with the original beam pattern of the probe, that was obtained in normal conditions of use according to prior art.

The figures only show one half of the beam pattern and further conveniently represent a dB standardized beam power pattern relative to the above defined u variable.

Figure 14:
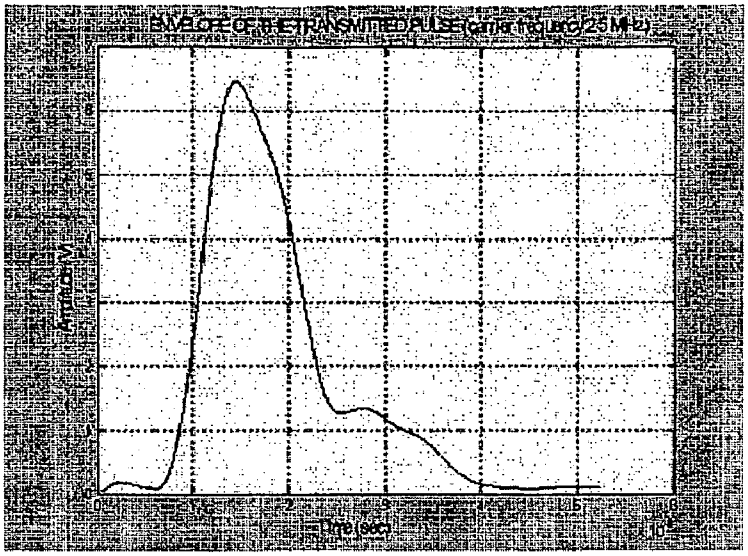
FIG. 14 shows the envelope of the waveform that forms the received pulse, and is used in beam pattern calculation.

It shall be noted that no optimization was effected for the transmit pulse generated according to prior art. FIG. 14 shows the envelope of the transmit pulse.

Figure 15:
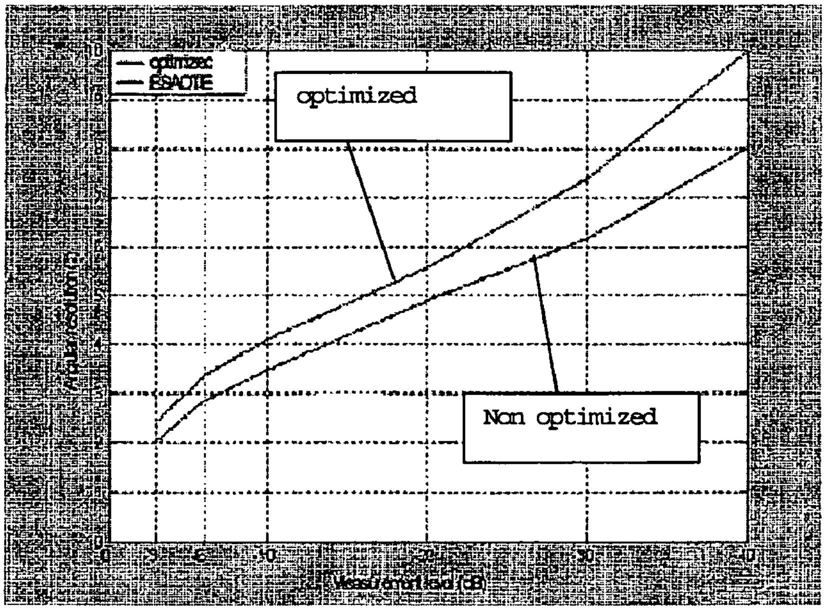
FIG. 15 is a chart that shows the comparison between the angular resolution of the receive signal as optimized according to this invention and the receive signal as obtained from prior art.

FIG. 15 further shows the considerable angular resolution improvement that was obtained by the receive pulse optimization according to the method of the present invention as compared with that obtained with the same probe used in the prior art modes.

The above clearly shows that the optimization according to the method of this invention also provides an optimal mechanical pressure of the transmit pulse, i.e. a constant pressure in a predetermined penetration depth range, which allows treatment of contrast agents, and prevents unexpected local peaks at depths different from the focusing depth, which might otherwise cause an at least partial destruction of contrast agent microbubbles and provide a beam pattern that ensures an optimal angular resolution and a reduced production of image artifacts. Even in its simplest form, wherein the transmit pulse is optimized by an appropriate amplitude weight vector for the contributions of the transducers to the comprehensive pulse, only for obtaining an optimal mechanical pressure, and wherein, on reception, the signal is optimized, still by an appropriate amplitude weight vector for the contributions of the transducers to the comprehensive signal only for obtaining an optimal beam pattern, the experimental results show that, as compared with prior art, better pressure profiles are obtained, as well as an effective reduction of artifacts and a better angular resolution.

Therefore, the simplified form of the inventive method allows to improve ultrasonic imaging performances while reducing the computational load required for determining the optimization weights.

What is claimed is:

1. A method of ultrasonic imaging comprising the step of optimizing one or more ultrasonic pulses in conjunction with ultrasonic imaging, wherein transmit pulses are generated from ultrasonic pulse contributions of each of a plurality of electroacoustic transducers, said transducers being grouped in an array and being individually triggered by electric excitation signals, said excitation signal being applied to each individual transducer of said array having a predetermined delay with respect to the application of the excitation signal that is applied to the other transducers of said plurality of transducers, and wherein a weight is applied to the excitation signal for each transducer for adjusting the amplitude of said excitation signal, characterized in the following steps:

defining an optimal desired mechanical pressure profile for said transmit pulses relative to the penetration depth of said transmit pulses within the body or object being examined as a function of at least amplitude weighting parameters for said transducers' contributions to said transmit pulses, and of the delays of excitation for transmission of individual pulse contributions of transducers, aimed at focusing comprehensive pulses on a scan line or band and at a certain penetration depth within the body or object under examination;

defining an ideal beam pattern for said transmit pulses relative to the propagation time or penetration depth within the body or object under examination as a function of at least amplitude weighting parameters for said transducers' contributions to said transmit pulses, and of delays of excitation delays for transmission of individual pulse contributions of transducers aimed at focusing comprehensive pulses on a scan line or band and at a certain penetration depth within the body or object under examination;

defining an energy function which depends on the difference between said ideal pressure profile and the actual pressure profile and between said ideal beam pattern and the actual beam pattern;

determining the minimum of said energy function;

determining said weighting parameters and said delays which correspond to the minimum of the energy function and applying said weighting parameters and said delays to said excitation signals for exciting said transducers to generate said comprehensive pulses.

2. A method as claimed in claim 1, characterized in that a further optimization variable for said transducers' pulse contributions is provided that forms said comprehensive pulses, which variable is the waveform of the pulse contribution generated by each transducer, that may be equal to or different from one transducer to the other.

3. A method as claimed in claim 1, characterized in that said energy function has the following general form:

$$E(W,\tau,\omega) = \int_z [Pcal_i(W,\tau,\omega,z) - Pdes(z)]^2 dz + \int_x\int [BPcal_i(W,\tau,\omega,z,x) - BPdes(z,x]^2\, dx dz$$

where:

Pdes(z) is the function that describes the desired pressure profile at the different penetration depths along the propagation axis x of the ultrasonic pulse, $Pcal_i(W,\tau,\omega,z)$ is the function that describes the pressure profile as determined from the weight vector, the delay vector and the waveform vector at the ith iteration of the minimization rector and at different penetration depths along the ultrasonic pulse propagation axis z, relative to the weight vector W, the delay vector $\tau$ and the waveforms of the pulse contributions generated by the transducers at $\omega$/;

BPdes(z,x) is the function that describes the desired beam pattern at the different penetration depths along the ultrasonic pulse propagation axis z relative to the weight vector W, the delay vector $\tau$ and the waveforms off the pulse contributions generated by the transducers $\omega$/;

$BPcal_i(W,\tau,\omega,z,x)$ is the function that describes the beam pattern as determined from the weight vector, the delay vector and the waveform vector at the ith iteration of the minimization vector and at the different penetration depths along the ultrasonic pulse propagation axis z, relative to the weight vector W, the delay vector $\tau$ and the waveforms of the pulse contributions generated by the transducers $\omega$.

4. A method as claimed in claim 3, characterized in that said energy function is discretized and integrals are transformed into a summation by assuming a certain approximation error margin.

5. A method as claimed in claim 4, characterized in that said two integrals of said energy function or the equivalent summations are multiplied by a weighting coefficient.

6. A method as claimed in claim 3, characterized in that said variable z may obviously change in a range of interest which spans the ultrasonic pulse focusing depth, or in a range in which the focusing depth is one of the upper or lower limits or is close to one of said limits whereas said variable x may be in a range that is equal to or larger than the whole extension of the transducer array along the x axis parallel to the transmit surface of said transducer array, or said range may be smaller than said extension of the transducer array along the x axis and of the same order of magnitude as a scan band corresponding to a few parallel and adjacent scan lines.

7. A method as claimed in claim 3, characterized in that said energy function is modified in such a manner as to include integration of the absolute values of differences, instead of the squared of the differences $Pcal_i$-Pdes and/or $BPcal_i$-Bpdes.

8. A method as claimed in claim 3, characterized in that said energy function is modified in such a manner as to include integration of the variables x and/or z upon limited intervals, to only consider one of said the main lobe or said side lobes.

9. A method as claimed in claim 3, characterized in that said energy function is modified in such a manner as to include the replacement of the desired pressure profile Pdes and/or the desired beam pattern BPdes with a constant.

10. A method as claimed in claim 9, wherein said constant may be null.

11. A method as claimed in claim 9, characterized in that said constant replaced in lieu of the desired profile pressure and/or the desired beam pattern BPdes corresponds to the average value of the desired pressure profile Pdes and/or the desired beam pattern BPdes over the integration interval being considered.

12. A method as claimed in claimed 3, characterized in that said energy function is modified in such manner as to include integration of any excess values of what was actually obtained with respect to what was desired.

13. A method as claimed in claim 3, characterized in that said energy function is modified in such a manner as to include replacement of the integral operator with a different operator.

14. A method as claimed in claim 13, wherein said different operator is a nonlinear operator.

15. A method as claimed in claim 13, wherein said different operator is a mean operator.

16. A method as claimed in claim 13, wherein said different operator is a maximum value operator.

17. A method as claimed in claim 3, characterized in that said energy function is modified in such a manner as to include an integration carried out with respect to polar coordinate variables.

18. A method as claimed in claim 3, characterized in that said energy function is modified in such a manner as to include an intergration carried out with respect to arbitrary variables, thereby proving an optimization that may apply to any steering angle of said scan line.

19. A method as claimed in claim 3, characterized in that said energy function is modified in such a manner as to include one or more of integration of the absolute values of differences; integration of the variables x and/or z upon limited intervals; the replacement of the desired pressure profile Pdes and/or the desired beam pattern Bpdes with a constant, wherein said constant may be null or may correspond to the average value of the desired pressure profile Pdes and/or the desired beam pattern BPdes over the integration interval being considered; integration of any excess values of what was actually obtained with respect to what was desired; replacement of the integral operator with a different operator, wherein said different operator is a nonlinear operator or a mean operator or a maximum value operator; an integration carried out with respect to polar coordinate variables; or an integration carried out with respect to arbitrary variables.

20. A method as claimed in claim 19, characterized in that said energy function is modified in such a manner as to include, for beam pattern optimization, a function that sums the integral of the square differences between obtained BPcal and desired Bpdes in the region of the side lobe, and the integral of the excess values with respect to a maximum level in the side lobe region.

21. A method as claimed in claim 19, characterized in that said energy function is modified in such a manner as to include, for pressure profile optimization, a function that considers pressure variance along the z axis.

22. A method as claimed in claim 1, characterized in that, as transducer excitation delays, typical ultrasonic pulse focusing delays may be used, which are constant in the energy function.

23. A method as claimed in claim 1, characterized in that, for all transducers, identical waveforms of respective contributions to said comprehensive pulses are defined.

24. A method as claimed in claim 1, characterized in that the minimization of said energy function is executed by using a stochastic algorithm or an evolutionary algorithm.

25. A method as claimed in claim 24, characterized in that minimization is executed by using a genetic algorithm.

26. A method as claimed in claim 24, characterized in that minimization is executed by using an algorithm named Simulated Annealing.

27. A method as claimed in claim 24, characterized in that minimization is executed by using an algorithm named Tabu search.

28. A method as claimed in claim 1, characterized in that it provides a combined transmit and receive optimization wherein amplitude weights of the individual pulse transducers' contributions are determined for only minimizing the mechanical pressure part of the energy function, whereas, upon reception, amplitude weights are applied to the signals emitted from the transducers, which weights are determined by only minimizing the beam pattern part of the energy function.

29. A method as claimed in claim 1, characterized in that, during transmission, the transmit pulse is optimized by minimization of the following function:

$$E(W,\tau,\omega)=\int_z [Pcal_i(W,\tau,\omega,z)-Pdes(z)]^2 dz$$

whereas, upon reception, the receive pulse is optimized by minimizing the following function:

$$E(W,\tau,\omega)=\int\int_x [BPcal_i(W,\tau,\omega,z,x)-BPdes(z,x]^2 dx dz$$

30. A method as claimed in claim 29, characterized in that the delays and/or waveforms are defined as constant whereas the transmit and/or receive optimization include the calculation of amplitude weights for individual transducers' contributions to the comprehensive transmit pulse and/or for individual transducers' contributions to the receive signal.

31. A method of ultrasonic imaging comprising the step of optimizing one or more ultrasonic pulses in conjunction with ultrasonic imaging, wherein receive pulses are generated from ultrasonic pulse contributions of each of a plurality of electroacoustic transducers, said transducers being grouped in an array and being individually triggered by electric excitation signals, said excitation signal being applied to each individual transducer of said array having a predetermined delay with respect to the application of the excitation signal that is applied to the other transducers of said plurality of transducers, and wherein a weight is applied to the excitation signal for each transducer for adjusting the amplitude of said excitation signal, characterized in the following steps:

defining an optimal desired mechanical pressure profile for said receive pulses relative to the penetration depth of said receive pulses within the body or object being examined as a function of at least amplitude weighting parameters for said transducers' contributions to said receive pulses, and of the delays of excitation for reception of individual pulse contributions of transducers, aimed at focusing comprehensive pulses on a scan line or band and at a certain penetration depth within the body or object under examination;

defining an ideal beam pattern for said receive pulses relative to the propagation time or penetration depth within the body or object under examination as a function of at least amplitude weighting parameters for said transducers' contributions to said receive pulses, and of delays of excitation delays for reception of individual pulse contributions of transducers aimed at focusing comprehensive pulses on a scan line or band and at a certain penetration depth within the body or object under examination;

defining an energy function which depends on the difference between said ideal pressure profile and the actual pressure profile and between said ideal beam pattern and the actual beam pattern;

determining the minimum of said energy function;

determining said weighting parameters and said delays which correspond to the minimum of the energy function and applying said weighting parameters and said delays to said excitation signals for exciting said transducers to generate said comprehensive pulses.

32. A method as claimed in claim 31, characterized in that a further optimization variable for said transducers' pulse contributions is provided that forms said comprehensive pulses, which variable is the waveform of the pulse contribution generated by each transducer, that may be equal to or different from one transducer to the other.

33. A method as claimed in claim 31, characterized in that said energy function has the following general form:

$$E(W,\tau,\omega)=\int_z [Pcal_i(W,\tau,\omega,z)-Pdes(z)]^2 dz + \int_x\int [BPcal_i(W,\tau,\omega,z,x)-BPdes(z,x]^2\,dx\,dz$$

where

Pdes(z) is the function that describes the desired pressure profile at the different penetration depths along the propagcation axis x of the ultrasonic pulse, $Pcal_i(W,\tau,\omega,z)$ is the function that describes the pressure profile as determined from the weight vector, the delay vector and the waveform vector at the ith iteration of the minimization vector and at different penetration depths along the ultrasonic pulse propagation axis z, relative to the weight vector W, the delay vector τ and the waveforms of the pulse contributions generated by the transducers ω/;

BPdes(z,x) is the function that describes the desired beam pattern at the different penetration depths along the ultrasonic pulse propagation axis z, relative to the weight vector W, the delay vector τ and the waveforms of the pulse contributions generated by the transducers ω/;

$BPcal_i(W,\tau,\omega,z,x)$ is the function that describes the beam pattern as determined from the weight vector, the delay vector and the waveform vector at the ith iteration of the minimization vector and at the different penetration depths along the ultrasonic pulse propagation axis z, relative to the weight vector W, the delay vector τ and the waveforms of the pulse contributions generated by the transducers ω.

34. A method as claimed in claim 33, characterized in that said energy function is discretized and integrals are transformed into a summation by assuming a certain approximation error margin.

35. A method as claimed in claim 34, characterized in that said two integrals of said energy function or the equivalent summations are multiplied by a weighting coefficient.

36. A method as claimed in claim 33, characterized in that said variable z may obviously change in a range of interest which spans the ultrasonic pulse focusing depth, or in a range in which the focusing depth is one of the upper or lower limits or is close to one of said limits whereas said variable x may be in a range that is equal to or larger than the whole extension of the transducer array along the x axis parallel to the transmit surface of said transducer array, or said range may be smaller than said extension of the transducer array along the x axis and of the same order of magnitude as a scan band corresponding to a few parallel and adjacent scan lines.

37. A method as claimed in claim 33, characterized in that said energy function is modified in such a manner as to include integration of the absolute values of differences, instead of the squared of the differences $Pcal_i$-Pdes and/or $BPcal_i$-Bpdes.

38. A method as claimed in claim 33, characterized in that said energy function is modified in such a manner as to include integration of the variables x and/or z upon limited intervals, to only consider one of said the main lobe or said side lobes.

39. A method as claimed in claim 33, characterized in that said energy function is modified in such a manner as to include the replacement of the desired pressure profile Pdes and/or the desired beam pattern BPdes with a constant.

40. A method as claimed in claim 39, wherein said constant may be null.

41. A method as claimed in claim 39, characterized in that said constant replaced in lieu of the desired profile pressure and/or the desired beam pattern BPdes corresponds to the average value of the desired pressure profile Pdes and/or the desired beam pattern BPdes over the integration interval being considered.

42. A method as claimed in claimed 33, characterized in that said energy function is modified in such manner as to include integration of any excess values of what was actually obtained with respect to what was desired.

43. A method as claimed in claim 33, characterized in that said energy function is modified in such a manner as to include replacement of the integral operator with a different operator.

44. A method as claimed in claim 43, wherein said different operator is a nonlinear operator.

45. A method as claimed in claim 43, wherein said different operator is a mean operator.

46. A method as claimed in claim 43, wherein said different operator is a maximum value operator.

47. A method as claimed in claim 33, characterized in that said energy function is modified in such a manner as to include an integration carried out with respect to polar coordinate variables.

48. A method as claimed in claim 33, characterized in that said energy function is modified in such a manner as to include an integration carried out with respect to arbitrary variables, thereby proving an optimization that may apply to any steering angle of said scan line.

49. A method as claimed in claim 33, characterized in that said energy function is modified in such a manner as to include one or more of integration of the absolute values of differences; integration of the variables x and/or z upon limited intervals; the replacement of the desired pressure profile Pdes and/or the desired beam pattern BPdes with a constant, wherein said constant may be null or may correspond to the average value of the desired pressure profile Pdes and/or the desired beam pattern Bpdes over the integration interval being considered; integration of any excess values of what was actually obtained with respect to what was desired; replacement of the integral operator with a different operator, wherein said different operator is a nonlinear operator or a mean operator or a maximum value operator; an integration carried out with respect to polar coordinate variables; or an integration carried out with respect to arbitrary variables.

50. A method as claimed in claim 49, characterized in that said energy function is modified in such a manner as to include, for beam pattern optimization, a function that sums the integral of the square differences between obtained Bpcal and desired Bpdes in the region of the side lobe, and the integral of the excess values with respect to a maximum level in the side lobe region.

51. A method as claimed in claim 49, characterized in that said energy function is modified in such a manner as to include, for pressure profile optimization, a function that considers pressure variance along the z axis.

52. A method as claimed in claim 31, characterized in that, as transducer excitation delays, typical ultrasonic pulse focusing delays may be used, which are constant in the energy function.

53. A method as claimed in claim 31, characterized in that, for all transducers, identical waveforms of respective contributions to said comprehensive pulses are defined.

54. A method as claimed in claim 31, characterized in that the minimization of said energy function is executed by using a stochastic algorithm or an evolutionary algorithm.

55. A method as claimed in claim 54, characterized in that minimization is executed by using a genetic algorithm.

56. A method as claimed in claim 54, characterized in that minimization is executed by using an algorithm named Simulated Annealing.

57. A method as claimed in claim 54, characterized in that minimization is executed by using an algorithm, named Tabu search.

58. A method as claimed in claim 31, characterized in that it provides a combined transmit and receive optimization wherein amplitude weights of the individual pulse transducers' contributions are determined for only minimizing the mechanical pressure part of the energy function, whereas, upon reception, amplitude weights are applied to the signals emitted from the transducers, which weights are determined by only minimizing the beam pattern part of the energy function.

59. A method as claimed in claim 31, characterized in that receive optimization is performed by minimizing the following energy function:

$$E(W) = \int_x [BPcal_i(W, \tau, \omega, z_0, x) - BPdes(z_0, z)]^2 dx$$

the so-called dynamic focus technique being applied upon reception, to maintain the focus of contributions from different depths.

60. A method as claimed in claim 31, characterized in that receive optimization is performed by minimizing the following energy function:

$$E(W) = \int_u [BPcal_i(W, \tau, \omega, u) - BPdes(u)]^2 du$$

where:

BPdes(u) is the function that describes the desired beam pattern as a function of an arbitrary variable u, whose possible values are of −2 to +2;

is the function that describes the beam pattern $BPcal_i(W, \tau, \omega, z)$ that was calculated on the basis of the weight vector, the delay vector and the waveform vector, at the ith iteration of the minimization algorithm and as a function of said arbitrary variable u;

and where the arbitrary variable u is defined as:

$u = \sin(\theta) - \sin(\theta_0)$ where $\theta_0$ is the steering direction; and $\theta$ is the arrival direction.

* * * * *